United States Patent
Petrich et al.

(10) Patent No.: US 6,413,087 B1
(45) Date of Patent: Jul. 2, 2002

(54) PACKAGED APPLICATOR ASSEMBLY

(75) Inventors: Robert W. Petrich, Woodbury; Bruce R. Broyles, Oakdale, both of MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/512,509

(22) Filed: Feb. 24, 2000

(51) Int. Cl.[7] .......................... A61C 5/04; A45D 40/24; B43K 5/00
(52) U.S. Cl. .................. 433/89; 433/215; 132/317; 401/202
(58) Field of Search .................. 433/89, 215; 401/119, 401/120, 124, 202, 262, 129; 132/317; 206/15.2, 15.3, 368, 63.5

(56) References Cited

U.S. PATENT DOCUMENTS

| | | |
|---|---|---|
| 550,763 A | 12/1895 | Osmun |
| 2,218,738 A | * 10/1940 | Boysen ...................... 206/63.5 |
| 3,230,574 A | 1/1966 | Kershaw |
| 3,345,674 A | 10/1967 | Groft |
| 3,369,543 A | 2/1968 | Ronco |
| 3,459,483 A | 8/1969 | Brastad |
| 3,464,775 A | 9/1969 | Beal |
| 3,613,697 A | * 10/1971 | Andrews ..................... 132/317 |
| 3,792,699 A | 2/1974 | Tobin et al. |
| 3,818,911 A | 6/1974 | Fournier |
| 3,918,435 A | 11/1975 | Beall et al. |
| 3,924,623 A | 12/1975 | Avery |
| 3,938,898 A | 2/1976 | Reitknecht |
| 4,805,646 A | * 2/1989 | Shimenkov ................. 433/89 |
| 4,828,419 A | * 5/1989 | Porter et al. ................ 132/317 |
| 4,952,204 A | 8/1990 | Korteweg |
| 5,001,803 A | * 3/1991 | Discko, Jr. .................. 433/215 |
| 5,006,004 A | * 4/1991 | Dirksing et al. ............. 401/262 |
| 5,097,853 A | 3/1992 | Nehashi |
| 5,229,061 A | 7/1993 | Van Dyke et al. |
| 5,283,924 A | 2/1994 | Kaminski et al. |
| 5,326,603 A | 7/1994 | Van Dyke et al. |
| 5,511,654 A | 4/1996 | de la Rocha |
| 5,522,795 A | 6/1996 | Green et al. |
| D377,216 S | 1/1997 | Mark |
| D377,525 S | 1/1997 | Mark |
| D377,526 S | 1/1997 | Mark |

(List continued on next page.)

FOREIGN PATENT DOCUMENTS

| | | |
|---|---|---|
| CA | 2244628 | 2/1999 |
| EP | 0411578 | 2/1991 |
| EP | 0 903 115 | 3/1999 |
| GB | 842965 | 8/1960 |
| GB | 1527544 | 10/1978 |
| WO | WO 9905987 | 2/1999 |

OTHER PUBLICATIONS

Microbrush, "Dispenser Series Disposable Applicator", 1 page.
Microbrush & Ultrabrush, "Dispenser Series Instructions for Assembly", 1 page.
Innovations, "In Unit Dose Infection Control Products" Huntington Medical Products, 4 pages.
Simplicity, Ease of Use, Versatility and Clever Design Define These New Packaging Systems, Gam–Med Packaging Corporation, 1 page.
Instructions for Opening the Squeeze–N–Twist Primer Dispenser, 3M Unitek, 8 pages.
Microbrush, Pro Touch, Disposable Touch–Up Microbrush.

*Primary Examiner*—Todd E. Manahan
(74) *Attorney, Agent, or Firm*—James D. Christoff

(57) ABSTRACT

An applicator assembly includes an applicator having a tip and a cap initially extending over the tip and detachably connected to the applicator. The applicator includes a flexible portion that can be bent in an arc as the cap is detached from the applicator in order to enhance access to the application site when needed. In preferred embodiments, the tip is supplied with a quantity of composition such as a dental composition, and as a result is especially advantageous for single patient use.

22 Claims, 1 Drawing Sheet

U.S. PATENT DOCUMENTS

| | | |
|---|---|---|
| D378,235 S | 2/1997 | Mark |
| 5,623,942 A | 4/1997 | Pestes et al. |
| D379,230 S | 5/1997 | Mark |
| 5,627,071 A | 5/1997 | Triva |
| D380,265 S | 6/1997 | Mark |
| 5,660,273 A | 8/1997 | Discko, Jr. |
| D385,964 S | 11/1997 | Mark |
| D392,465 S | 3/1998 | Mark |
| 5,780,305 A | 7/1998 | Chisum |
| D397,441 S | 8/1998 | Mark |
| 5,794,632 A | 8/1998 | Gueret |
| 5,826,600 A | 10/1998 | Rowe et al. |
| D403,768 S | 1/1999 | Mark et al. |
| 5,860,806 A | 1/1999 | Pranitis, Jr. et al. |
| 5,862,818 A | 1/1999 | Marinelli |
| 5,874,045 A | 2/1999 | Chisum |
| D408,080 S | 4/1999 | Mark |
| D409,914 S | 5/1999 | Mark |
| D413,381 S | 8/1999 | Mark |
| 5,989,229 A | 11/1999 | Chiappetta |
| D417,394 S | 12/1999 | Mark |
| 5,996,780 A | 12/1999 | Gurrera |
| D419,068 S | 1/2000 | Mark |
| 6,010,462 A | 1/2000 | Stoermer, III |
| 6,227,737 B1 * | 5/2001 | Lightfoot .................... 132/317 |

* cited by examiner

PACKAGED APPLICATOR ASSEMBLY

BACKGROUND OF THE INVENTION

1. Field of the Invention

This invention relates to a packaged applicator assembly that includes an applicator for applying a composition to a surface. The invention also relates to a method for preparing an applicator for use, and a method for applying a dental composition to tooth structure.

2. Description of the Related Art

Applicators for applying compositions to surfaces are in widespread use in a variety of medical, commercial and household applications. Typical examples of such applicators include brushes and swabs having an overall stick-like configuration. Applicators that are relatively inexpensive represent a significant convenience to the user, in that the applicator can be disposed of after a single use.

In some instances, disposable applicators are individually packaged in closed, sealed containers. Individually packaged applicators are an advantage in medical and dental operatories because sterility of the applicator can be assured until such time as the applicator is removed from the package in preparation for use. Examples of known packaged applicators include swabs that are contained between two sheets of a plastic or paper film, and swabs that are contained within a plastic tube or casing.

Another type of disposable applicator that is known in the art has been available from Microbrush Corporation of Grafton, Wisconsin under the name "Microbrush". This applicator has an elongated handle that is connected to an outer tip. The tip is flocked with a number of small fibers that facilitate spreading of a composition over the application site. The handle includes a reduced-diameter flexible portion that can be bent past its yield point to a desired angular orientation to facilitate placement of the composition in certain instances, such as when it is necessary to apply the composition to an area where access is limited.

In some procedures, the composition to be applied by the applicator is provided in bulk containers. In those instances, the users may elect to dip the swab or brush tip of the applicator directly into the container in order to coat the tip with a small quantity of the composition. The tip is then removed from the container and moved across the desired surface in order to transfer the composition from the tip to the surface.

However, the practice of dipping the applicator tip directly into a bulk container is not satisfactory in many medical and dental applications due to the possibility of cross-contamination between patients. For example, if the applicator is used in a dental procedure to apply an adhesive to the surface of tooth structure, the practitioner may unknowingly transfer infectious disease from one patient to another if the applicator is returned to the bulk container after initial use in the oral cavity. The issue of cross-contamination can be avoided by using a new applicator in those instances where additional composition is needed, but such practice represents an additional expense and also requires a certain amount of time for retrieving, opening and preparing a new packaged applicator for use.

The problems of cross-contamination as mentioned above can be avoided by use of a dispensing well or pad. For example, in dental procedures a small quantity of composition is dispensed from the bulk container onto the well or pad, and the tip of the applicator is then used to transfer the composition from the well or pad to the patient's tooth structure. Such practice avoids the need for returning the applicator to the bulk container so that issues of cross-contamination between patients can be avoided. Once the procedure has been completed, the well or pad is disposed of or cleaned for reuse.

In recent years, there has been increased interest in packaged, disposable applicators having a tip that is pre-supplied with a quantity of a composition. These prepackaged applicators are a significant advantage in that the time that would otherwise be associated with handling of a bulk container and a dispensing well or pad can be avoided. Moreover, such packaged applicators are a particular advantage when used with compositions that are messy or that are considered hazardous.

One example of a packaged swab assembly is described in U.S. Pat. No. 4,952,204 and includes a swab having a cotton bud that is pre-supplied with a quantity of composition. The swab is contained within a plastic sleeve that includes a relatively small diameter cylindrical handle portion at one end, a substantially larger diameter receptacle portion at the opposite end and a transition portion of compound configuration between the small diameter portion and the larger diameter portion. This patent indicates that when the sleeve is squeezed at the intersection between its larger diameter receptacle portion and its transition portion, the material of the sleeve will snap, crack or tear such that the swab is exposed for use upon removal of the receptacle portion.

Although a wide variety of applicators and application methods are known in the art as demonstrated by the foregoing, there exists a need for an improved applicator that is especially adapted for use in regions where access is limited. Such an applicator would be particularly useful in certain dental applications where a composition must be applied to remote posterior regions of the patient's oral cavity.

SUMMARY OF THE INVENTION

The present invention relates to a packaged applicator assembly that represents a significant improvement over previously known applicators and applicator assemblies. The assembly of the invention includes an applicator and a cap, and the applicator includes a flexible portion. As the cap is detached from the applicator, the flexible portion is bent in an arc in order to facilitate use of the applicator, particularly in areas where access is limited.

In one preferred embodiment of the invention, a tip of the applicator bears a quantity of a composition such as a dental adhesive that is initially covered by the cap. As the cap is removed, the flexible portion of the applicator can be bent to any one of a number of angles in order to facilitate spreading the adhesive on the patient's tooth structure of interest. As such, there is no need to attempt to bend the applicator by hand once the cap has been removed, and potential contact of the adhesive with the practitioner's fingers or with other structure can be avoided.

In more detail, the present invention in one aspect is directed toward an applicator assembly that comprises an applicator including a handle and an elongated shaft connected to the handle. The shaft includes a tip remote from the handle and a flexible portion located between the tip and the handle. The assembly further includes a cap extending over the tip and at least part of the flexible portion. The cap is detachably connected to the applicator. The flexible portion of the applicator can be bent as the cap is detached from the applicator.

In another aspect, the present invention is directed toward a method of preparing an applicator for use. The method includes the acts of covering a tip of the applicator with a cap, and connecting the cap to the applicator. The method also includes the act of detaching the cap from the applicator, wherein the act of detaching the cap from the applicator includes the act of bending a shaft of the applicator.

The present invention is also directed toward a method of applying a dental composition to tooth structure. The method includes the act of providing an applicator having a handle, a tip and a shaft, wherein the shaft is located between the handle and the tip. The method also includes the acts of covering the tip with a cap and placing a dental composition on the tip. The method additionally includes the act of removing the cap from the tip, wherein the act of removing the cap from the tip includes the act of bending the shaft. The method also includes the act of contacting the tip with tooth structure in order to transfer at least a portion of the composition to the tooth structure.

Preferably, the applicator and the cap are disposed of after a single use. As such, the invention is particularly useful for dental compositions where issues of cross-contamination might otherwise present a problem. The invention is also beneficial when used to dispense and apply a composition that cannot be feasibly dispensed from a bulk container over a period of time, such as a composition that rapidly cures upon exposure to the atmosphere or to ambient light. Optionally, the cap includes a reservoir of the composition that enables the user to rewet the tip by reinserting the tip in the cap, an especially useful advantage in instances where an additional application is needed.

These and other aspects of the invention are described in more detail below and are illustrated in the accompanying drawings.

DETAILED DESCRIPTION OF THE PREFERRED EMBODIMENTS

Figure 1:
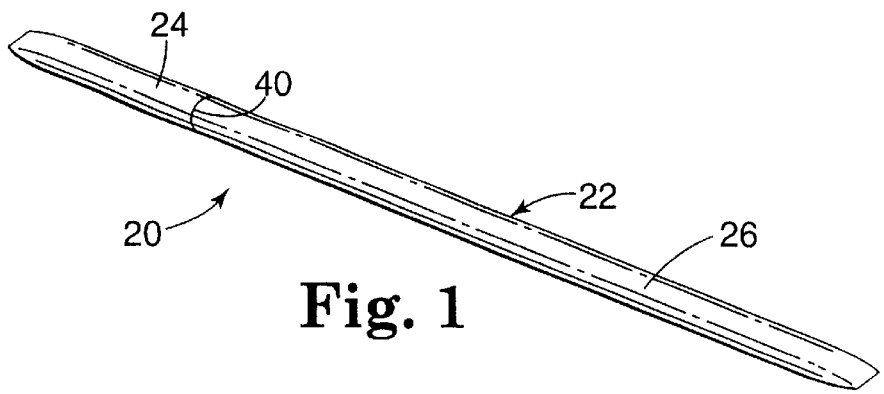
FIG. 1 is a perspective view of an applicator assembly that is constructed in accordance with one embodiment of the invention.
Figure 2:
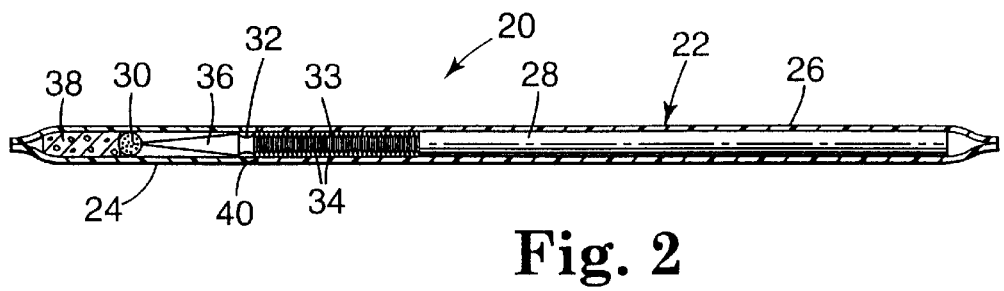
FIG. 2 is a side cross-sectional view of the applicator assembly illustrated in FIG. 1.
Figure 3:
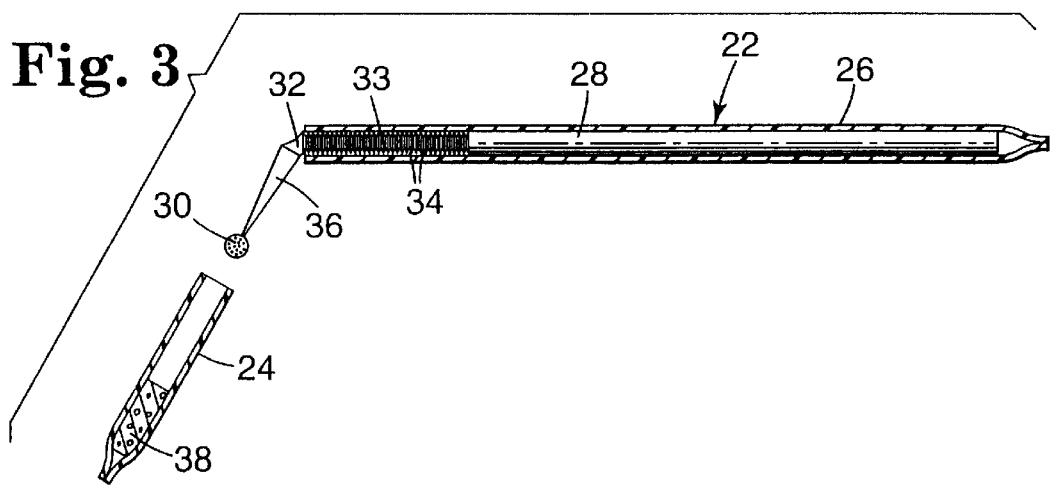
FIG. 3 is a side cross-sectional view of the applicator assembly depicted in FIGS. 1 and 2 after a cap of the assembly has been detached from an applicator to expose a tip of the applicator.

An applicator assembly according to one embodiment of the invention is broadly designated by the numeral 20 in FIGS. 1–3. The assembly 20 includes an applicator 22 as well as a cap 24 that is detachably connected to the applicator 22. Initially, and as shown in FIG. 1, the assembly 20 has an overall cylindrical configuration along the majority of its length and has a straight, longitudinal central reference axis.

The applicator 22 of the assembly 20 has an outer handle 26 and an elongated shaft 28 that is connected to the handle 26. In the particular embodiment shown, the shaft 28 extends through almost the entire length of the handle 26. The shaft 28 includes an outer tip 30 that is located in a position remote from the handle 26. Optionally, and as illustrated in FIGS. 2 and 3, the tip 30 has a generally spherical configuration, although other shapes are also possible.

Preferably, but not necessarily, the tip 30 includes a material that facilitates spreading of a composition across the surface to which the composition is to be applied. The material may be of any suitable structure that is compatible with the composition and functions to distribute the composition over the receiving surface. Suitable materials include small bristles or fibers that serve as a brush and that are applied to all or only part of the tip 30.

Optionally, fibers can be applied to the tip 30 by a flocking process. The flocking can be carried out by any technique known in the art. Preferably, the flocked fibers define small interstitial spaces that can advantageously fill with the composition, and retain and suspend a small amount of the composition for efficient application to the surface of interest. The fibers preferably also allow relatively uniform application of the composition over the surface regardless of whether the surface is irregular, rough or smooth, and apply the composition in the same way as a brush would. If used in a dental procedure, the outwardly extending fibers permit the composition to be applied easily to side and overhanging surfaces of a tooth cavity as well as to the bottom of the tooth cavity.

Alternatively, other types of material may be applied to the tip 30 for facilitating spreading of the composition across a surface. Examples of such other materials include an open cell foam material such as polyurethane foam or synthetic sponge. Additional examples of suitable materials include woven and non-woven fabrics, gauzes and the like. Microstructured surfaces could also be employed, including microstructured surfaces that are integrally formed as part of the tip 30.

The shaft 28 of the applicator 22 also includes a flexible portion 32 that is located between the tip 30 and the handle 26. The flexible portion 32 is deformable by finger pressure past its yield point to any one of a number of angular orientations, and once bent will substantially self-remain in a bent orientation without returning to its initially straight orientation. Although some amount of return to its initially straight position is possible, particularly if the flexible portion is made of a resilient material, it is preferred that the flexible portion 32 remain in approximately the same angular orientation to which it is bent after the bending pressure is released.

One method of making the flexible portion 32 involves the provision of one or more grooves that serve to facilitate bending of the shaft 28. In the example shown in the drawings, the flexible portion 32 includes a single groove that circumscribes the shaft 28. The groove lies in a reference plane that is oriented perpendicular to the longitudinal axis of the assembly 20. However, other constructions are also possible, including the use of a series of grooves, a section of reduced cross-sectional area of another shape or an articulated joint to facilitate bending.

The shaft 28 also includes a gripping portion 33 located rearwardly of the flexible portion 32. The gripping portion 33 is made of a series of grooves 34 that are uniformly spaced apart from each other. The gripping portion 33 is optional and is not gripped in use of the applicator 22 since it is located within the hollow handle 26.

In the embodiment shown in the drawings, the shaft 28 also includes a tapered portion 36 that is located between the flexible portion 32 and the tip 30. The tapered portion 36 has a generally conical configuration, and advantageously provides clearance in areas adjacent the tip 30 when used in certain applications. For example, if the tip 30 is used to apply a dental composition to overhanging tooth surfaces, the tapered portion 36 facilitates application of the composition in areas beneath that overhanging surface.

The cap 24 has an inner cavity that surrounds the tip 30, the flexible portion 32 and the tapered portion 36 when the cap 24 is connected to the applicator 22. Preferably, the cap 24 provides a reservoir for composition to be dispensed and applied by the tip 30. Optionally, the reservoir includes a porous material that facilitates retention of the composition in the cap 24 so that the composition does not drip from the cap 24 when the cap 24 is inverted after it is detached from the applicator 22.

Preferably, the reservoir is a compressible porous material such as a synthetic sponge 38 as shown in FIG. 2. An example of a suitable material for the sponge 38 is polyurethane. However, other materials, including woven and non-woven fabrics and gauzes, are also possible.

Preferably, the sponge 38 has suitable dimensions and is located in the cap 24 such that the tip 30 slightly compresses the sponge 38 when the cap 24 is connected to the applicator 22. Such construction ensures that the tip 30 will remain wetted with the composition carried by the sponge 38. Moreover, if additional composition is needed once the composition on the tip 30 has been exhausted, the tip 30 can be re-inserted into the cap 24 in order to contact the sponge 38 again and transfer additional composition to the tip 30.

The cap 24 is connected to the applicator 22 by any suitable detachable connection known in the art. An example for a suitable detachable connection is a line of weakness 40 that circumscribes the assembly 20 in a region overlying the flexible portion 32. Preferably, the line of weakness 40 is a frangible area of reduced cross-sectional thickness that initially integrally interconnects the cap 24 to the handle 26. However, other detachable connections are also possible, including the use of an adhesive, a friction fit or a pressure sensitive tape that initially retains the cap 24 in secure connection to the applicator 22.

In use, the assembly 20 is grasped by the user, preferably with one hand on the handle 26 and the other hand on the cap 24. Next, the applicator 22 and the cap 24 are moved relative to each other in an arc such that the longitudinal axis of the applicator 22 moves from a position collinear with the longitudinal axis of the cap 24 to an orientation at a non-zero angle relative to the longitudinal axis of the cap 24. During this bending movement, the line of weakness 40 fractures along all or at least a portion of its circumscribing length. Such bending motion of the cap 24 relative to the applicator 22 will also cause the flexible portion 32 to bend.

The cap 24 is then moved away from the handle 26 in a direction along the length of the applicator 22 to uncover the tip 30. The flexible portion 32, having moved past its yield point during the bending motion as the cap is removed, remains in its deformed, bent orientation as illustrated in FIG. 3 after the cap 24 is separated from the applicator 22. If the user is not satisfied with the resultant angular orientation, the cap 24 can be temporarily replaced onto the applicator 24 so that the user's fingers need not contact the tip 30 or the composition during additional bending movements.

FIGS. 1 and 2 illustrate the assembly 20 as it initially appears while FIG. 3 depicts the assembly after the cap 24 has been detached from the handle 26 and the shaft 28 has been bent in the region of the flexible portion 32. As can be appreciated, the applicator assembly 20 is an advantage in that bending of the applicator 22 can be carried out simultaneously with removal of the cap 24. Such construction represents a time savings for the user, in that a separate step of bending the applicator 22 after removal of the cap 30 is not normally required.

Additionally, bending of the applicator 22 simultaneously with detachment of the cap 24 enables the applicator 22 to be bent to any desired angular orientation without fear of contamination of the tip 30, the tapered portion 36, the flexible portion 32 or the composition on the tip 30. Such construction avoids the need to grasp the uncovered tip 30 with one hand for bending the flexible portion 32, or the need to press the tip 30 against some other surface for bending the flexible portion 32. The tip 30 and the composition remain safely covered by the cap 24 until the desired angular orientation is attained.

Optionally, the applicator 22 may be flexible in areas other than the flexible portion 32, such as in areas of the tapered portion 36. However, if the cap 24 is detached from the applicator 22 by relative bending movement, the cap 24 will tend to retain the forward section of the applicator 22 that is located within the cap 24 during bending in a straight orientation so long as the cap 24 fits closely over the forward section of the applicator. As a result, the applicator 22 only bends to any substantial degree in these instances in areas near the line of weakness 40. Advantageously, the handle 26 and the cap 30 provide leverage for facilitating bending of the applicator.

A preferred method of making the assembly 20 is carried out using a length of cylindrical tubing and placing a sponge (such as sponge 38) near one end of the tubing. That end of the tubing is then placed between a pair of movable, heated jaws (or a heated platen and anvil assembly) that heat-seals the outer end region of the tubing. The jaws are then moved toward each other and press against opposite sides of the tubing. During this pressing and heat-sealing, an adjacent end section of the sponge is compressed between inner walls of the tubing adjacent the heat seal to retain the sponge in place. Next, a slender, hollow probe is inserted into the tubing through its open end and a quantity of composition is dispensed onto the sponge.

Subsequently, an applicator stick such as the "Microbrush" brand applicator described above is placed within the tubing such that the tip contacts the sponge and slightly compresses the sponge. In that position, the open, outer end of the tubing remote from the tip extends just slightly beyond the applicator stick surrounded within. A pair of heated jaws are then pressed against opposite sides of the remaining open end region of the tubing in order to heat seal the opening and also to mechanically capture by friction fit the adjacent end of the applicator stick.

The tubing described in the method above may be made of any material that provides sufficient strength and stiffness to the resultant assembly during shipping, storage, handling and use including the acts of removing the cap as described above. The selected material should also be compatible with the composition contained in the sponge and provide satisfactory shelf life performance. An example of a suitable material for the tubing is polyethylene.

Optionally, the tubing can have a laminate construction made of one or more layers of different material in instances where one type of material may provide superior packaging characteristics in one aspect and another material may provide superior packaging characteristics in another aspect. For example, a two layer laminate tubing might be selected having a first layer that is made of a material that provides superior barrier properties such as resistance to fluid and vapor transmission. In this example, the second layer may be made of a material that provides superior strength and stiffness properties, to ensure that the resultant assembly 20 is strong and somewhat flexible and yet can be reliably opened when desired with a crisp snapping effect by fracturing along the line of weakness 40.

The initially straight configuration of the applicator assembly 20 is an advantage during manufacturing, shipping and storage in that a large number of the assemblies 20 can be packaged in a compact, tight array with little wasted space. Moreover, the initially straight configuration of the assembly 20, in combination with the flexible portion 32, allows the user to bend the applicator 22 to a selected, preferred orientation that may be best suited for the task at hand. Such construction is beneficial in contrast to applicators that are pre-bent by the manufacturer, since the angle selected by the manufacturer may not be optimal or even satisfactory in every situation.

Optionally, the assembly 20 can be opened without bending the applicator in instances where the user desires to keep the applicator 22 in a straight configuration for use. To open the assembly 20 without bending the applicator 22, the cap 24 can be twisted in an arc about its longitudinal axis while holding the handle 26 stationary.

Preferably, the tip 30 bears an amount of the composition when removed from the cap 24 that is sufficient to complete the chosen task. If desired, however, an additional amount of composition can be transferred to the tip 30 when needed by placing the tip 30 back into the cap 24 and into contact with the sponge 38. Preferably, the material of the tip 30 has an affinity for the composition to facilitate transfer of the composition from the sponge 38 to the tip 30.

Figure 4:
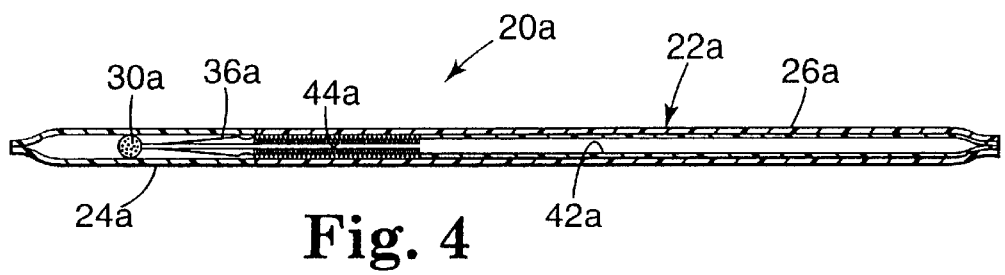
FIG. 4 is a side cross-sectional view of an applicator assembly that is constructed in accordance with another embodiment of the invention.

Another embodiment of the invention is illustrated in FIG. 4, wherein an applicator assembly 20a comprises an applicator 22a and a cap 24a. Except as described below, the assembly 20a is identical to the assembly 20 and as such a detailed description of the various similar features, elements and aspects shall not be repeated.

The applicator 22a includes a hollow shaft 28a and has an inner chamber 42a that extends along its length. The chamber 42a includes a small passageway 44a that extends through a tapered portion 36a as well as through a tip 30a. Optionally, the assembly 20a may have a somewhat larger outer diameter in comparison to a preferred diameter of the assembly 20 in order to provide sufficient space for the chamber 42a. A handle 26a extends over a portion of the shaft 28a. Optionally, the initially open, rear end region of the shaft 28a is heat-sealed shut within a surrounding heat sealed region of the handle 26a in order to close the chamber 42a once the composition has been added.

A quantity of composition is initially received in the chamber 42a. Preferably, the tip 30a also bears some quantity of the same composition when the applicator 22a is within the cap 24a so that the applicator 22a is ready for immediate use as soon as the cap 24a is removed. In this embodiment, a sponge within the cap 24a (such as the sponge 38 described above) is optional.

In use, the cap 24a is detached from the applicator 22a in the manner described above in connection with the assembly 20. However, once the composition carried by the tip 30a has been somewhat depleted, the user can replenish the supply of composition on the tip 30a by squeezing the walls of the handle 26a together. Compression of the walls of the handle 26a reduces the amount of space in the chamber 42a and as a consequence causes a portion of the composition in the chamber 42a to be urged through the passageway 44a and onto the tip 30a.

The applicator assemblies described above are suitable for use with a wide variety of compositions for various procedures. The composition could be a liquid, semi-liquid, gel, paste or powder. A particularly preferred composition is a one-part dental adhesive that cures upon exposure to light. An example of a suitable dental adhesive is "Single Bond" brand adhesive from 3M Company. Other suitable compositions include dental etchants, sealants and primers. As used herein, the word "dental" includes all fields of dentistry including orthodontic and endodontic treatment.

A number of options and alternatives are possible to the applicator assemblies described above. For example, the handles described above could be provided with a flange or collar in order to assure that the composition does not drip onto the user's fingers when the tip is held in an upwardly position during use. A number of other options will also be apparent to those skilled in the art. Accordingly, the invention should not be deemed limited to the specific examples that are described in detail above, but instead only by a fair scope of the claims that follow along with their equivalents.

What is claimed is:

1. An applicator assembly comprising:

an applicator including a handle and an elongated shaft connected to the handle, the shaft including a tip remote from the handle and a flexible portion located between the tip and the handle;

a cap extending over the tip and at least part of the flexible portion, the cap being detachably connected to the applicator, and wherein the flexible portion of the applicator can be bent as the cap is detached from the applicator; and a quantity of composition received on the tip, wherein the composition is a dental composition selected from the group of dental adhesives, dental sealants, dental primers and dental etchants.

2. An applicator assembly comprising:

an applicator including a handle and an elongated shaft connected to the handle, the shaft including a tip remote from the handle and a flexible portion located between the tip and the handle;

a cap extending over the tip and at least part of the flexible portion, the cap being detachably connected to the applicator, and wherein the flexible portion of the applicator can be bent as the cap is detached from the applicator; and a reservoir located in the cap and containing a quantity of composition, wherein the reservoir comprises a sponge, wherein the sponge contacts the tip when the cap is connected to the applicator, wherein the sponge is at least partially compressed when the cap is connected to the applicator, and wherein the composition is a dental composition.

3. An applicator assembly comprising:

an applicator including a handle and an elongated shaft connected to the handle, the shaft including a tip remote from the handle and a flexible portion located between the tip and the handle;

a cap extending over the tip and at least part of the flexible portion, the cap being detachably connected to the applicator, wherein the flexible portion of the applicator can be bent as the cap is detached from the applicator, wherein the shaft has an inner chamber, wherein the tip has an internal passageway in communication with the chamber; and a quantity of composition received in the chamber.

4. An applicator assembly comprising:

an applicator including a handle and an elongated shaft connected to the handle, the shaft including a tip remote from the handle and a flexible portion located between the tip and the handle; and a cap extending over the tip and at least part of the flexible portion, the cap being detachably connected to the applicator, wherein the flexible portion of the applicator can be bent as the cap is detached from the applicator, wherein the cap has a heat-sealed outer end region, wherein the cap includes a sponge and wherein a section of the sponge is captured in the heat-sealed outer end region.

5. An applicator assembly comprising:

an applicator including a handle and an elongated shaft connected to the handle, the shaft including a tip remote from the handle and a flexible portion located between the tip and the handle; and a cap extending over the tip and at least part of the flexible portion, the cap being detachably connected to the applicator, wherein the flexible portion of the applicator can be bent as the cap is detached from the applicator, wherein the shaft extends through at least part of the handle, wherein the handle includes a heat-sealed outer end region, and wherein a section of the shaft is captured in the heat-sealed outer end region.

6. A method of preparing an applicator for use comprising the acts of:

covering a tip of the applicator with a cap;

connecting the cap to the applicator; and detaching the cap from the applicator, wherein the act of detaching the cap from the applicator includes the act of bending a flexible portion of a shaft of the applicator past its yield point.

7. A method of preparing an applicator for use according to claim 6 wherein the act of bending a shaft of the applicator is carried out simultaneously with the act of detaching the cap from the applicator.

8. A method of preparing an applicator for use according to claim 6 wherein the act of detaching the cap from the applicator includes the act of fracturing a frangible connection between the cap and the applicator.

9. A method of preparing an applicator for use according to claim 6 wherein the act of connecting the cap to the applicator includes the act of establishing a barrier that resists vapor and moisture transfer from the atmosphere to a tip of the applicator received in the cap.

10. A method of preparing an applicator for use according to claim 6 wherein the applicator has an initially straight orientation with a longitudinal axis, and wherein the act of detaching the cap from the applicator includes the act of moving the cap away from the applicator in a direction that is substantially parallel to the longitudinal axis.

11. A method of preparing an applicator for use according to claim 6 and including the act of placing a quantity of composition on the tip of the applicator that is located within the cap when the cap is connected to the applicator.

12. A method of preparing an applicator for use according to claim 6 wherein the act of connecting the cap to the applicator includes the act of compressing a resilient, porous material that is located within the cap.

13. A method of preparing an applicator for use according to claim 6 and including the act of squeezing the applicator in order to urge composition located in a chamber of the applicator toward a tip of the applicator.

14. A method of applying a dental composition to tooth structure comprising the acts of:

providing an applicator having a handle, a tip and a shaft, wherein the shaft is located between the handle and the tip;

covering the tip with a cap;

placing a dental composition on the tip;

removing the cap from the tip, wherein the act of removing the cap from the tip includes the act of bending the shaft; and contacting the tip with tooth structure in order to transfer at least a portion of the composition to the tooth structure.

15. A method of applying a dental composition to tooth structure according to claim 14 wherein the act of removing the cap from the tip includes the act of detaching the cap from the handle.

16. A method of applying a dental composition to tooth structure according to claim 15 wherein the act of detaching the cap from the handle includes the act of fracturing a frangible connection between the cap and the handle.

17. A method of applying a dental composition to tooth structure according to claim 14 and including the act of squeezing the handle in order to urge dental composition located in a chamber of the applicator to the tip.

18. A method of applying a dental composition to tooth structure according to claim 14 wherein the act of contacting the tip with the tooth structure includes the act of moving a plurality of bristles of the tip across the tooth structure.

19. A method of applying a dental composition to tooth structure according to claim 14 wherein the act of contacting the tip with the tooth structure include the act of moving a porous material of the tip across the tooth structure.

20. A method of applying a dental composition to tooth structure according to claim 14 and including the act of inserting the tip back into the cap after the cap has been removed from the tip in order to transfer additional dental composition to the tip.

21. A method of applying a dental composition to tooth structure according to claim 20 wherein the act of inserting the tip back into the cap includes the act of contacting the tip with a porous material in the cap.

22. A method of applying a dental composition to tooth structure according to claim 14 wherein the act of covering the tip with a cap includes the act of establishing at least a partial seal between the cap and the applicator in order to provide a barrier between the composition on the tip and the atmosphere.

* * * * *